(12) United States Patent
Pezzulli

(10) Patent No.: US 12,558,487 B2
(45) Date of Patent: Feb. 24, 2026

(54) COLLAPSIBLE SYRINGE PLUNGER AND SYRINGE INCORPORATING SAME

(71) Applicant: Anthony C. Pezzulli, Fairview, TX (US)

(72) Inventor: Anthony C. Pezzulli, Fairview, TX (US)

( * ) Notice: Subject to any disclaimer, the term of this patent is extended or adjusted under 35 U.S.C. 154(b) by 140 days.

(21) Appl. No.: 17/392,201

(22) Filed: Aug. 2, 2021

(65) Prior Publication Data

US 2023/0037112 A1    Feb. 2, 2023

(51) Int. Cl.
*A61M 5/315*    (2006.01)

(52) U.S. Cl.
CPC .... *A61M 5/31513* (2013.01); *A61M 5/31505* (2013.01); *A61M 2005/31518* (2013.01)

(58) Field of Classification Search
CPC .......... A61M 5/31501; A61M 5/31505; A61M 5/31511; A61M 5/31515; A61M 5/31513; A61M 2005/31518; A61M 2005/31506; A61M 2005/31508
See application file for complete search history.

(56) References Cited

U.S. PATENT DOCUMENTS

| | | | |
|---|---|---|---|
| 3,572,337 A | 3/1971 | Schunk | |
| 5,501,670 A | 3/1996 | Sak | |
| D383,205 S | 9/1997 | Pagay et al. | |
| D618,347 S | 6/2010 | Bradshaw | |
| D638,123 S | 5/2011 | Kosinski et al. | |

| | | | |
|---|---|---|---|
| D713,525 S | 9/2014 | Oguro et al. | |
| D750,768 S | 3/2016 | Davidian et al. | |
| D819,203 S | 5/2018 | Grunhut et al. | |
| D844,776 S | 4/2019 | Combes et al. | |
| D895,792 S | 9/2020 | Ho | |
| 10,842,940 B1 | 11/2020 | Pusateri | |
| D911,519 S | 2/2021 | Newlove et al. | |
| 11,801,349 B2 * | 10/2023 | Murray .............. | A61M 5/31511 |
| 2009/0318880 A1 * | 12/2009 | Janish ................ | A61M 5/31511 604/228 |
| 2011/0046569 A1 * | 2/2011 | Lum .................. | A61M 5/31515 604/219 |

(Continued)

FOREIGN PATENT DOCUMENTS

| | | |
|---|---|---|
| CN | 302830739 | 5/2014 |
| GB | 90020373660002 | 5/2012 |

(Continued)

OTHER PUBLICATIONS

Prior art syringe at least as early as Aug. 1, 2021, photograph.

(Continued)

*Primary Examiner* — Michael J Tsai
*Assistant Examiner* — Justin L Zamory
(74) *Attorney, Agent, or Firm* — Braxton Perrone, PLLC; Gregory Perrone; Bobby W. Braxton

(57)    ABSTRACT

A plunger for a syringe comprises a stem portion with a longitudinally extending groove that receives an extension portion. The extension portion sits at least partially within the groove when a space-saving, collapsed configuration is desired. When a user is ready to elongate the plunger and/or use a syringe containing the plunger, the extension portion can slide within the groove to lengthen the plunger until a locking mechanism is engaged.

20 Claims, 3 Drawing Sheets

(56)                    References Cited

U.S. PATENT DOCUMENTS

2018/0264195 A1      9/2018   Hopkins

FOREIGN PATENT DOCUMENTS

| HK | 15017360002 | 5/2012 |
| JP | 1683487 | 4/2021 |

OTHER PUBLICATIONS

"AAProTools: Aspirating Syringe CW Type." Found online at Amazon.com, Oct. 19, 2022, Reference dated Nov. 19, 2016, Retrieved from https://www.amazon.com/AAProTools-Aspirating-Syringe-C-Green-Instruments/dp/B07SMG222F.

AAProTools: Dental Auto Passive Syringe, found online at amazon. com, Oct. 19, 2022, Reference date Nov. 19, 2016, retrieved from https ://www.amazon.com/ AA Pro Tools-Aspirating-Anesthetic-American-European/dp/B08WRYVM 1 N/.

CYNAMED: Premium Aspiring Dental Syringes, found online at Amazon.com, Oct. 19, 2022, reference dated Apr. 26, 2018, retrieved from https://www.amazon.com/ASPIRING-SYRINGES-ANES-THETIC-INSTRUMENTS-CYNAMED/dp/B07CPJG77F/.

Fixfans: BGA Solker Paste Flux Mate Booster Plunger Dispenser Tool, found online at amazon.com, Oct. 19, 2022, reference date Aug. 20, 2018, Retrieved from https://www.amazon.com/Booster-Plunger-Dispenser-Aluminum-Propulsion/dp/B08HN2755Q.

* cited by examiner

COLLAPSIBLE SYRINGE PLUNGER AND SYRINGE INCORPORATING SAME

BACKGROUND OF THE INVENTION

Technical Field

The present invention relates generally to a plunger for a syringe and a syringe incorporating the plunger.

History of Related Art

Syringe devices comprising a snuggly fitting plunger in a vessel with an attached needle at one end are known to be used for the withdrawal and injection of different medications and nutrients. Mechanical operation is generally the same. The plunger of the syringe is used to apply pressure through a cylindrical storage reservoir, forcing liquid either into or out of the reservoir. In the delivery of a liquid, the syringe device is often separately stored in a closed position within packaging, while a liquid is stored in a separately sealed vial. Consequently, when the time comes to administer a liquid medication, one must remove packaging and seals prior to forcing liquid into the syringe from the separate vial before injecting the medication. A life-saving medication may require quick injection and it may be difficult to wrestle with packaging and accurate dosing. While pre-filled syringes do exist, these can take up valuable space when other medications must be at hand.

SUMMARY

There is a need for a space-saving syringe that can be easily stored and quickly set up for quick administration. The collapsible plunger and the syringe comprising the plunger described herein provide these benefits and more.

Below is a simplified summary of this disclosure meant to provide a basic understanding of the method(s) described herein. This is not an exhaustive overview and is not intended to identify key or critical elements or to delineate the scope of the description. Its sole purpose is to present some concepts in a simplified form as a prelude to the more detailed description below.

In one aspect, a plunger for a syringe comprises a base for receiving a plunger seal tip and a stem portion extending from the base, the stem portion comprising a longitudinally extending groove. A correspondingly shaped extension portion extends from a first end to a second end and fits within the groove. In some embodiments, the groove is U-shaped with two side walls and a middle wall between the side walls. The groove further comprises an interlocking mechanism therein to vary the length of the plunger and lock it into an elongated position when desired.

In another aspect, a collapsible plunger for a syringe comprises a base; a stem portion extending from the base, said stem portion comprising a longitudinally extending groove; and an extension portion slidably mounted within the groove, the extension portion comprising a first end within the groove; wherein the stem portion and the extension portion comprise an interlocking mechanism within the groove. The interlocking mechanism causes the extension portion and the stem portion to engage and lock in place in an extended configuration.

In another aspect, a syringe comprises a barrel and a collapsible plunger within the barrel, the collapsible plunger comprising a stem portion and an extension portion slidably mounted within the stem portion, wherein the stem portion comprises a base for receiving a plunger seal tip and a groove longitudinally extending from on an opposing surface of the base, and wherein the extension portion and the stem portion comprise an interlocking mechanism within the groove.

In any of the above embodiments, the stem portion comprises two longitudinally extending grooves and the extension portion comprises two corresponding arms extending from an end piece of the extension portion, each arm slidably mounted within one of the two grooves. In one embodiment, the grooves may be parallel. In one embodiment, the arms diverge from a grip end piece of the extension portion.

In any of the above embodiments, the groove of the stem portion comprises a projection and the extension portion comprises a corresponding notch.

Other aspects, embodiments, and features of this disclosure will become apparent in the following written description and accompanying drawings.

BRIEF DESCRIPTION OF THE DRAWINGS

The novel features believed characteristic of the invention are set forth in the appended claims. The invention itself, however, as well as further objectives and advantages thereof, will be best understood by reference to the following detailed description of illustrative embodiments when read in conjunction with the accompanying drawings, wherein:

DETAILED DESCRIPTION

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition is expressly set forth in the specification in a definitional manner that directly and unequivocally provides the special definition for the term or phrase.

The terms "including," "comprising," "having," and variations thereof mean "including but not limited to," unless expressly specified otherwise. When used in the appended claims, in original and amended form, the term "comprising" is intended to be inclusive or open-ended and does not exclude any additional, unrecited element, method, step or material. The term "consisting of" excludes any element, step or material other than those specified in the claim. Unless specifically set forth herein, the terms "a", "an", and "the" are not limited to one of such elements, but instead mean "at least one," unless otherwise specified. The term "about" as used herein refers to the precise values as subsequently indicated as well as to values that are within statistical variations or measuring inaccuracies.

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Figure 1:
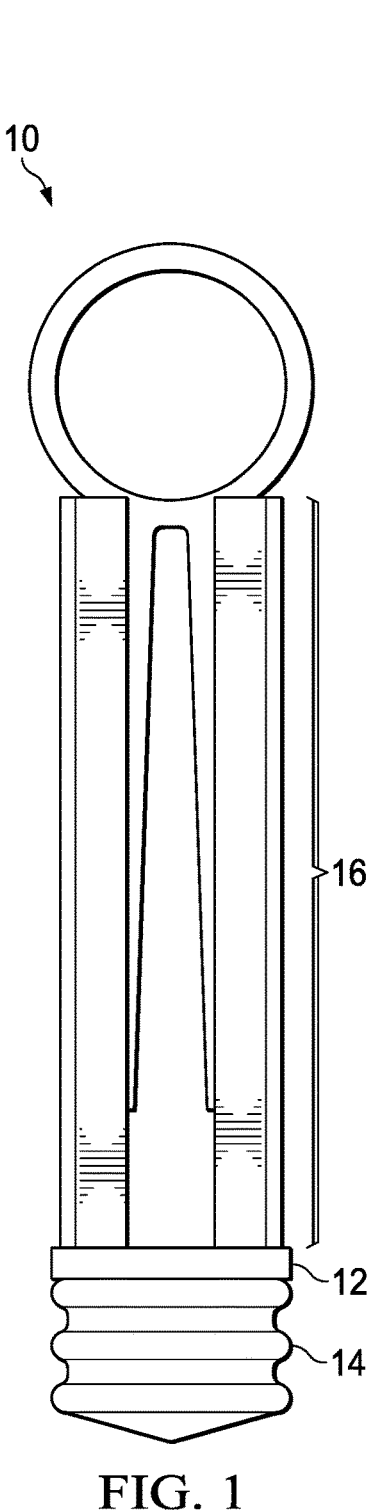
FIG. 1 depicts a collapsed view of one embodiment of a plunger described herein.

FIG. 1 depicts one embodiment of a plunger 10 in a closed or collapsed configuration, with a stem portion 16 extending from a base 12 and an extension portion 20 within the stem portion 16. A plunger seal tip or plug 14 may be attached to a bottom side of the base 12 on the stem portion by any means known in the art. The plunger seal tip 14 forms a seal between the plunger and the barrel or syringe vessel, preventing any leakage of fluid to the plunger during operation of a syringe to dispense fluid into or out of the syringe. Correct sizing for the base 12 and/or seal tip 14 can be determined based on the size of the syringe used and for the desired seal.

The extension portion 20 comprises a first end within the groove 18 and a second end outside the groove 18. In some embodiments, the first end sits near the base 12 in the collapsed configuration. The second end comprises a grip 24, which may rest on top of the stem portion when in a collapsed configuration. In one embodiment, the grip 24 comprises an opening for a finger or objected to be inserted for operating a syringe. The grip may also comprise a flange or similar mechanism, if desired, to hold the plunger and bear the load when forcing a liquid into or out of a syringe.

Figure 2:
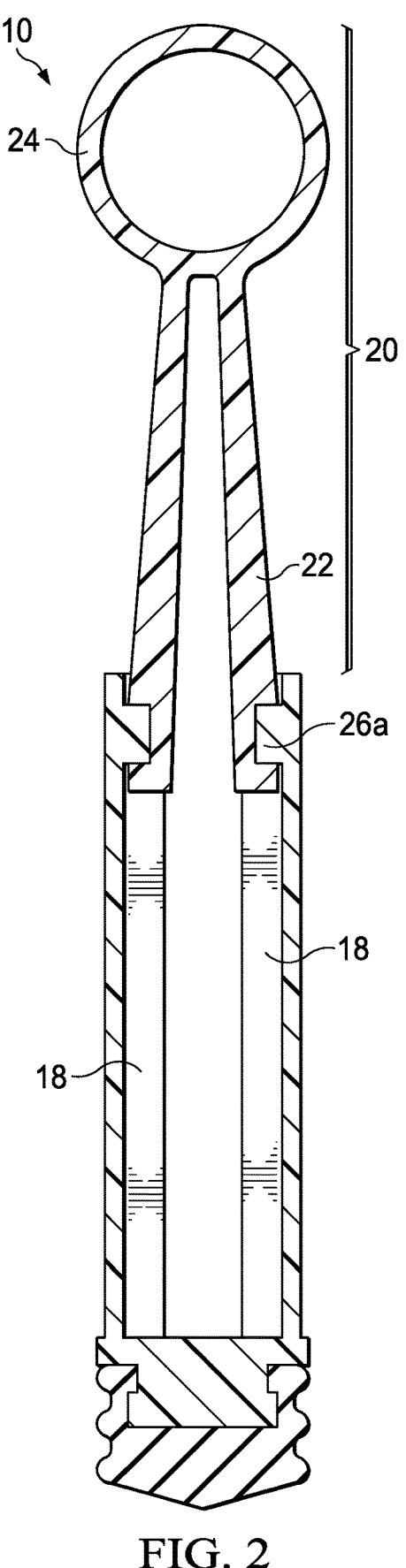
FIG. 2 depicts a cross-sectional view of one embodiment of a plunger in an extended configuration.

FIG. 2 depicts a cross sectional view of the plunger 10 in an extended configuration, with the extension portion 20 pulled away from the base 12, and a locking mechanism 26, further described below, in an engaged position.

Figure 3:
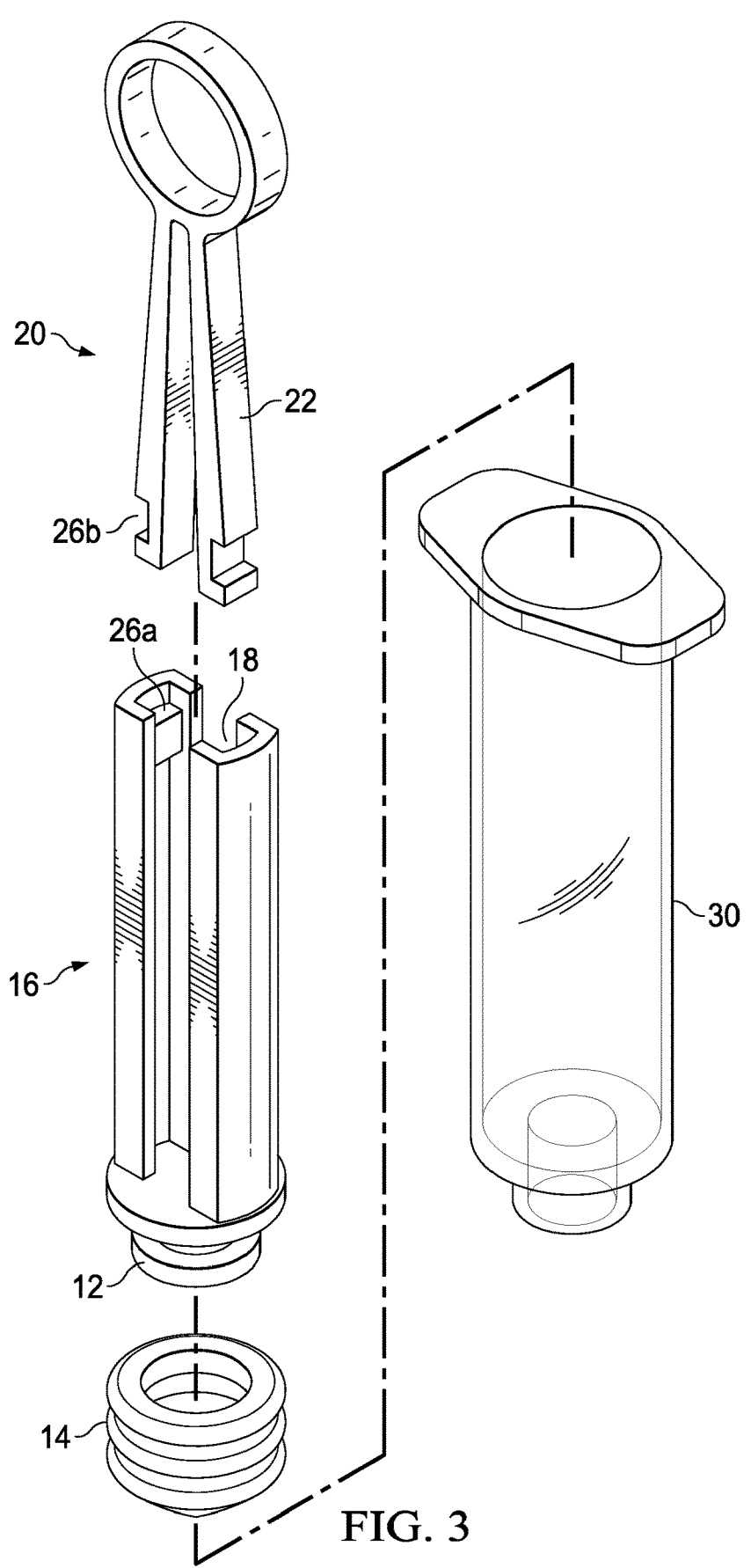
FIG. 3 depicts an exploded perspective view of one embodiment of a plunger described herein.

As perhaps best shown in FIG. 3, in one embodiment, the stem portion 16 comprises two longitudinally extending slots or grooves 18 in which each arm 22 of the extension portion 20 slidably fits. In one embodiment, the groove 18 extends from the base 12 to an opposite end of the stem portion 16. An arm 22 slides within the groove 18 to nest within the groove 18 in a collapsed configuration. The groove 18 essentially acts as a track or guide for the arm 22 of an extension portion 20, with the arm 22 sliding within the groove to vary the length of the plunger. In one embodiment, the groove 18 is U-shaped along its length, with two sidewalls and a middle wall between the two side walls to form an elongated channel. However, in other embodiments, the shape of the groove may be semi-circular, semi-cylindrical, triangular, rectangular, or any configuration so long as the arm of the extension portion is also adapted to fit within the groove. In certain embodiments, the stem portion 16 comprises two spaced apart grooves, each groove for receiving an arm 22 of an extension portion 20. In one embodiment, the stem portion 16 comprises two sets of walls with the grooves facing one another. In some embodiments, the stem portion 16 may also comprise a single structure with one or more grooves therein to receive the extension portion, such as a solid or semi-solid column with grooves therein.

FIGS. 2 and 3 best depict an embodiment of the extension portion 20 comprising two arms 22 extending from the second end or grip 24 down to the first end of the extension portion. In certain embodiments, the arms 22 are diverging from the second end 24, starting at or near a common point and diverging towards a corresponding groove in the stem portion 16. In one embodiment, the arms 22 are substantially parallel after diverging at an angle. In some embodiments, the arms 22 diverge at an angle of less than 40 degrees, depending, to some extent, on the size of the stem portion and syringe barrel. The length of the extension portion 20 and arms 22 may vary, depending on the length of the groove and the desired length of a lengthened configuration of the plunger. In some embodiments, the extension portion 20 and the stem portion 16 are separate, discrete pieces that work together. Thus, in some embodiments, a plunger may comprise or consist of two pieces—a stem portion and an extension portion.

Figure 4:
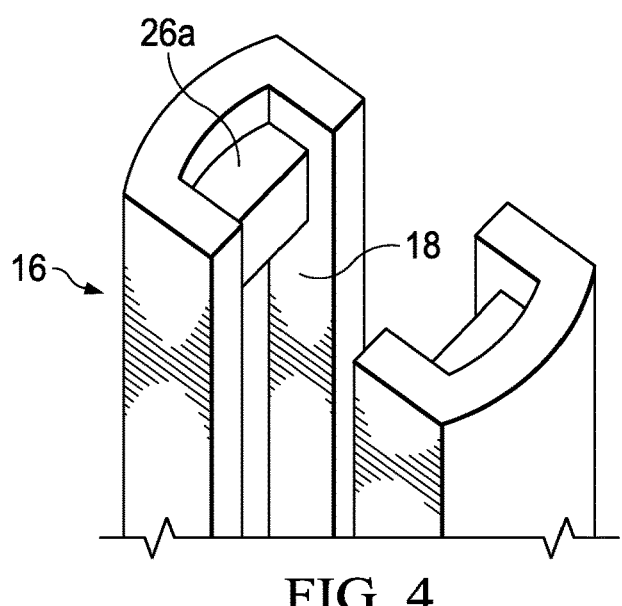
FIG. 4 depicts a close-up perspective view of a groove according to one embodiment.

Within the groove 18, the plunger 10 further comprises a locking mechanism wherein the extension portion 20 engages the stem portion 16 in an extended configuration in which the plunger is elongated and locked in position. In some embodiments, the locking mechanism 26 comprises a notch and a projection that fits within the notch. With reference to FIGS. 2-4, the stem portion 16 comprises a projection 26a within the groove 18. In some embodiments, projection 26a is inset inside of groove 18 to keep the extension portion 20 from being able to slip out from the track or groove 18. An arm 22 of the extension portion 20 comprises a notch 26b that fits within the projection 26a, engaging the projection 26a when the extension portion 20 is pulled away from the base 12. In some embodiments, the notch 26a is located at an end opposite the second end 24. In some embodiments, the projection 26b is located at the end of the stem portion 16 opposite the base. Generally, the notch and projection may be located on along any portion of the groove 18 and arm 22, depending on a desired length of the plunger in its extended, locked configuration.

Figure 5:
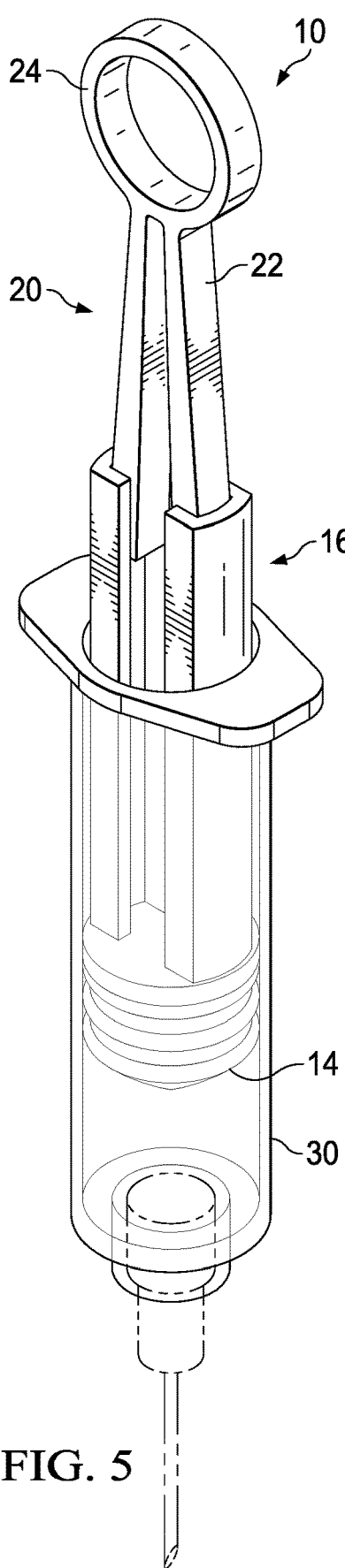
FIG. 5 depicts a perspective view of one embodiment of an assembled syringe described herein.

The exact size of the plunger may be varied, depending upon the diameter and length of the syringe barrel, as best shown by FIG. 5 in its generally assembled form, with one embodiment of the plunger in an extended, locked configuration. Any number of needles or attachments known in the art may be used. In some embodiments, the size of the base 12 may dictate the size of the groove and corresponding extension portions. Generally, the base is circular to fit within most syringe barrels. The base may also comprise a generally flat plane, depending upon how the plunger seal tip is attached to provide for the seal in the syringe.

As a space-saving device, the syringe plunger may be in a closed, or shortened, position until lengthening of the plunger is desired. Once application of force or pressure to a liquid inside the reservoir tube is desired, the plunger can be extended by pulling out the extension portion, thereby lengthening the plunger and locking the plunger in an extended position. To collapse the syringe in a space-saving configuration, the locking mechanism is disengaged to slide the extension portion back down a groove of the stem portion. In some embodiments, two arms of the extension portion may be squeezed together to disengage the locking mechanism. Once the extension portion is pulled away from the base and locked into a lengthened position, the plunger can be used to force liquid in and/or out of a syringe.

The device described herein may be free of any component or limitation not specifically described or depicted herein. For example, the collapsible plunger and syringe disclosed herein may be free of springs, screws, coils, and complicated mechanisms. While the invention has been particularly shown and described with reference to certain embodiments, it will be understood by those skilled in the art that various changes in form and detail may be made therein without departing from the spirit and scope of the invention.

ADDITIONAL DISCLOSURE

The following clauses are offered as further description of the disclosed invention.

Clause 1. A plunger for a syringe comprising a base for a plunger seal tip and a stem portion extending from the base, the stem portion comprising at least one longitudinally extending groove.

Clause 2. The plunger of clause 1 or any of clauses 3-7 comprising an extension portion extending from a first end to a second end, the extension portion slidably mounted with the groove.

Clause 3. The plunger of any preceding clause or any of clauses 4-7 wherein the second end comprises a grip.

Clause 4. The plunger of any preceding clause or any of clauses 5-7 wherein the groove comprises an interlocking mechanism.

Clause 5. The plunger of any preceding clause or any of clauses 6-7 wherein the interlocking mechanism comprises a notch and an engaging projection within the groove.

Clause 6. The plunger of any preceding clause or clause 7 wherein the stem portion comprises the projection and the extension portion comprises the notch.

Clause 7. The plunger of any preceding clause wherein the stem portion comprises two longitudinally extending grooves and the plunger further comprises an extension portion comprising two arms that each slidably mount within one of the two grooves.

Clause 8. A collapsible plunger for a syringe comprising:
a base for receiving a plunger seal tip;
a stem portion extending from the base, said stem portion comprising at least one longitudinally extending groove;
an extension portion slidably mounted within the groove, the extension portion comprising a first end within the groove and a second end opposite the first end;
wherein the stem portion and the extension portion comprise an interlocking mechanism within the groove.

Clause 9. The collapsible plunger of clause 8 or any of clauses 10-13 wherein the interlocking mechanism comprises a notch and a projection.

Clause 10. The collapsible plunger of clause 9 wherein the projection engages the notch in a locked lengthened configuration.

Clause 11. The collapsible plunger of any of clauses 8-10 or any of clauses 12-13 wherein the second end is outside the groove.

Clause 12. The collapsible plunger of any of clauses 8-11 or clause 13 wherein the longitudinally extending groove extends from a surface of the base to an opposite end of the stem portion.

Clause 13. The collapsible plunger of any of clauses 8-12 wherein the stem portion comprises two longitudinally extending grooves and the extension portion comprises two arms extending from the end piece, each arm slidably mounted within one of the two longitudinally extending grooves.

Clause 14. A syringe comprising a plunger, wherein the plunger comprises a base for a plunger seal tip and a stem portion extending from the base, the stem portion comprising at least one longitudinally extending groove.

Clause 15. The syringe of clause 14 or any of clauses 16-20 wherein the plunger further comprises an extension portion extending from a first end to a second end, wherein at least a portion of the extension portion is slidably mounted within the groove.

Clause 16. The syringe of any of clauses 14-15 or any of clauses 17-20 wherein the second end comprises a grip.

Clause 17. The syringe of any of clauses 14-16 or any of clauses 18-20 wherein the groove extends from a surface of the base to an opposite end of the stem portion.

Clause 18. The syringe of any of clauses 14-17 or any of clauses 19-20 wherein the plunger comprises a locking mechanism within the groove, the locking mechanism locking the extension portion and the stem portion together in an extended configuration.

Clause 19. The syringe of any of clauses 14-18 or clause 20 wherein the plunger comprises two longitudinally extending grooves, each groove for receiving an arm of an extension portion, the extension portion slidably mounted within the stem portion to achieve a collapsed configuration.

Clause 20. The syringe of any preceding claim wherein the grip comprises an opening for a finger or an object to be inserted therethrough to slide the extension portion away from the base, thereby extending a length of the plunger.

What is claimed is:

1. A plunger for a syringe comprising a base for a plunger seal tip and a stem portion extending from the base, the stem portion comprising two longitudinally extending grooves, each of said grooves forming an elongated channel facing one another; and an extension portion comprising a length substantially similar to that of the stem portion and two arms defining the extension portion extending substantially the entire length of the extension portion from a first end of the extension portion to a second end of the extension portion, each arm diverging from the second end of the extension portion to the first end and the first end of each arm fitting within one of the elongated channels, wherein the extension portion is slidably mounted within the elongated channel to vary the length of the plunger.

2. The plunger of claim 1 wherein the extension portion and the stem portion are separate pieces.

3. The plunger of claim 1 wherein the second end comprises a grip opposite the base, and wherein the second end sits outside the grooves of the stem portion.

4. The plunger of claim 1 wherein each of the grooves comprise an interlocking mechanism that interlocks with each of the arms.

5. The plunger of claim 4 wherein the interlocking mechanism comprises an engaging projection within the groove, and wherein each of the arms comprises a notch.

6. The plunger of claim 5 wherein the stem portion comprises the projection and the extension portion comprises the notch.

7. A collapsible plunger for a syringe comprising:
a base for receiving a plunger seal tip;
a stem portion extending from the base, said stem portion comprising two parallel longitudinally extending grooves, each of said grooves forming an elongated channel facing one another from the base to an opposite end of the base of the stem portion;
an extension portion slidably mounted within the grooves, the extension portion comprising a first end within each of the grooves and a second end opposite the first end, the second end outside the stem portion, wherein the extension portion comprises a length substantially similar to that of the stem portion and two arms diverging from the second end, the arms defining the extension portion and extending substantially an entire length of the extension portion from the first end of the extension portion to a terminal surface of the second end of the extension portion, and each arm nesting with a corresponding one of the elongated channels in a collapsed configuration.

8. The collapsible plunger of claim 7 wherein the stem portion and the extension portion comprise an interlocking mechanism that locks the collapsible plunger into an elongated position when engaged.

9. The collapsible plunger of claim 8 wherein the interlocking mechanism is within the elongated channels.

10. The collapsible plunger of claim 7 wherein the second end is outside the grooves.

11. A syringe comprising a barrel and a collapsible plunger within the barrel, wherein the collapsible plunger comprises a stem portion and an extension portion, the stem portion comprising a base and two parallel grooves longitudinally extending from the base, each groove forming a channel and each channel facing one another, and wherein the extension portion comprises two arms, the two arms having a length substantially similar to that of the stem portion and defining the extension portion and extending substantially an entire length from a first end and a terminal surface of a second end, the first end of each arm slidable mounted within each corresponding groove and the second end located outside the syringe, each arm diverging at an angle from the second end of the extension portion.

12. The syringe of claim 11 wherein the second end comprises a grip.

13. The syringe of claim 11 wherein the plunger comprises a locking mechanism within the groove, the locking mechanism locking the extension portion and the stem portion together in an extended configuration.

14. The syringe of claim 12 wherein each of the grooves of the stem portion is U-shaped along a length of the stem portion, said length from the base of the stem portion to the second end opposite the base, wherein both the stem portion and the extension portion fit within the barrel in a collapsed configuration.

15. The syringe of claim 11 wherein each of the grooves comprises a U-shape along a length of the stem portion, said length extending from the base of the stem portion to an opposite end of the stem portion.

16. The syringe of claim 15 wherein the opposite end of the stem portion comprises a locking mechanism that locks the extension portion and the stem portion together in an extended configuration.

17. The syringe of claim 12 wherein the grip comprises a ring.

18. The collapsible plunger of claim 7 wherein the arms of the extension portion nest entirely within the enlongated channels of the stem portion in a collapsed configuration.

19. The collapsible plunger of claim 7 wherein each of the grooves comprises a U-shape along a length of the stem portion, said length extending from the base of the stem portion to an opposite end of the stem portion.

20. The collapsible plunger of claim 7 wherein the second end comprises a grip, said two arms of the extension portion diverging from the grip.

\* \* \* \* \*